United States Patent [19]

Germond et al.

US005545554A

[11] Patent Number: 5,545,554

[45] Date of Patent: Aug. 13, 1996

[54] *LACTOBACILLUS BULGARICUS* HAVING DECREASED ACID PRODUCTION AND/OR IMPROVED AROMA AND FLAVOR PRODUCTION

[75] Inventors: Jacques E. Germond, Crissier; Herbert Hottinger; Olivier Mignot, both of Blonay; Beat Mollet, Mollie-Margot, all of Switzerland; Koichiro Tsuda, Nishiakashikita-Machi Akashi, Japan

[73] Assignee: Nestec S.A., Switzerland

[21] Appl. No.: 286,880

[22] Filed: Aug. 5, 1994

[30] Foreign Application Priority Data

Aug. 6, 1993 [EP] European Pat. Off. .............. 93202320

[51] Int. Cl.$^6$ ...................................... C12N 1/20
[52] U.S. Cl. ...................... 435/252.9; 435/190; 435/200; 435/853; 426/61

[58] Field of Search ................................ 435/170, 252.9, 435/853

[56] References Cited

U.S. PATENT DOCUMENTS

| 4,411,991 | 10/1983 | Hirrakawa et al. | 435/42 |
| 4,560,661 | 12/1985 | Katsumata et al. | 435/183 |
| 4,605,622 | 8/1986 | Hasegawa et al. | 435/182 |
| 5,382,438 | 1/1995 | Hottinger et al. | 426/43 |
| 5,416,020 | 5/1995 | Severson et al. | 435/252.9 |

*Primary Examiner*—Herbert J. Lilling
*Attorney, Agent, or Firm*—Knobbe Martens Olson & Bear

[57] ABSTRACT

The present invention concerns *Lactobacillus bulgaricus* wherein the lactate dehydrogenase activity is lower than 50%, preferably lower than 10%, of the lactate dehydrogenase activity of *Lactobacillus bulgaricus* wild type strain.

The present invention concerns also the food composition comprising said *Lactobacillus bulgaricus*.

9 Claims, 3 Drawing Sheets

LACTOBACILLUS BULGARICUS HAVING DECREASED ACID PRODUCTION AND/OR IMPROVED AROMA AND FLAVOR PRODUCTION

FIELD OF THE INVENTION

The present invention concerns a *Lactobacillus bulgaricus* having decreased acid production and/or improved aroma and flavor production.

The present invention is related also to a food composition, especially a mild yoghurt or mild yoghurt like products comprising the *Lactobacillus bulgaricus* according to the invention.

BACKGROUND OF THE INVENTION AND STATE OF THE ART

Yoghurt results from growth association of the two lactic acid bacteria, *Streptococcus thermophilus* and *Lactobacillus bulgaricus*. They grow together in milk where they ferment lactose, which is present at about 40–50 g per liter, to lactate. The whole fermentation usually takes 3 to 5 hours at 40° C. and lowers pH from neutral to about 4.2. Upon storage at 4°–12° C. for several days, the pH then drops further to values below 4.0. Parallel to this increased acidity an appearance of bitterness develops and greatly degrades the organoleptic quality of the product.

It is *L. bulgaricus* which produces the typical yoghurt aroma during the fermentation process. Therefore, yoghurt missing or having a reduced titer of metabolic active *L. bulgaricus* cells miss the aroma components of the typical yoghurt. Thus, such yoghurt (or yoghurt like products) can be very neutral, i.e. flat in taste. This problem is particularly eminent for the production of mild or very mild yoghurt, which as a consequence of the limited growth rate of *L. bulgaricus* tend to lose a lot of their aroma.

The number of consumers that prefer the milder yet aromatic and flavorful yoghurt seems to have increased in recent years. Therefore, the control method of the acid production on the milk fermentation process and the preventing of the post-acidification, which is the pH dropping during the storage, were truly desired by yoghurt producers. Up to now, several methods or starter strain improvements have been suggested to control the acidification and post-acidification of yoghurt. Most of them are to reduce the number of the active cells in starter culture or to eliminate living cells from the finished product by pasteurizing. Alternatively, low acidifying strains are being used.

U.S. Pat. No. 4,734,361 (Murao et al.) describes such a *Lactobacillus bulgaricus* strain (OLL 1074) which has been deposited in Japan under the number FERM BP 1041.

This variant shows a weak tendency towards formation of lactic acid at lower temperatures.

By employing this variant, it is possible to produce a fermented milk or lactic acid beverage in which post-acidification at a lower temperature is reduced.

U.S. Pat. No. 5,071,763 (Somkuti et al.) describes that mutant strains of *Streptococcus thermophilus* having defective lactose transport systems and having a phenotype gluS, lacS−, sucS+ and βgal+ are effective for use in processes where the hydrolysis of lactose is important. Thermostability of these strains as well as production of β-gatactosidase allow lactose hydrolysis prior to and during pasteurization. These organisms provide the food industry with improved methods of making reduced lactose dairy products.

In *L. bulgaricus*, lactose is taken up by the lactose permease system and cleaved by the β-galactosidase into its two moieties, glucose and galactose. Glucose is metabolized further to pyruvate, most of which is converted to lactate by the D-lactate dehydrogenase (D-LDH).

However, some of the pyruvate is decarboxylated to acetaldehyde, an important yoghurt aroma component, or channeled into other pathways resulting in aroma or aroma precursor elements.

Thomas et al. (J. of Bacteriology, May 1974, p. 329–333) and Smart et al. (Applied and Environmental Microbiology, March 1987, p. 533–541) describe that for Lactic streptococci, homolactic fermentation can be changed to heterolactic fermentation by reducing the LDH activity.

Payton et al. (FEMS Microbiology letters, 26, 1985, p. 333–336) describe that the LDH minus mutant of *Bacillus stearothermophilus* increase the amount of the ethanol production (following fermentation of glucose), whereas they lose the ability to produce lactate.

The document Journal of Bacteriology (vol. 144; no. 1, 1980, pages 217–221) shows that when the strain *Lactobacillus bulgaricus* NLS-4 grows anaerobically in continuous culture with limiting glucose, a shift in the pH of the medium from the acidic to the alkaline range causes this normally homofermentative bacterium to catabolize glucose in a heterofermentative fashion. The change in the fermentation is accompanied by a decrease in lactate dehydrogenase (LDH) biosynthesis in alkaline conditions.

However, yoghurt is an acid medium and this document does not suggest that it is possible to obtain a decrease in lactate dehydrogenase biosynthesis in acid conditons.

SUMMARY OF THE INVENTION

The present invention aims to provide a *Lactobacillus bulgaricus* having improved aroma and flavor production.

Another aim of the present invention is to provide a *Lactobacillus bulgaricus* also having reduced acidification and post-acidification.

A further aim of the present invention is to obtain a food composition, preferably a mild yoghurt or a mild yoghurt like product comprising said *Lactobacillus bulgaricus*, having an increased aroma and flavor production and/or a reduced acidification and post-acidification, preferably at low and high temperature.

DETAILED DESCRIPTION OF THE INVENTION

The present invention concerns a *Lactobacillus bulgaricus* having a more reduced lactate dehydrogenase (LDH) activity than of the wild type strain Lfi5 (deposited under the name CNCM I-800 at the Institut Pasteur, 28 rue du Docteur ROux, 75024 PARIS Cedex 15, FRANCE).

Advantageously, said lactate dehydrogenase activity is lower than 50%, preferably lower than 10%, of the lactate dehydrogenase activity of this wild type strain.

Advantageously, the lactate dehydrogenase activity is lower than 250 units, preferably lower than 150. units, of enzyme activity/10 ml culture.

The lactate dehydrogenase activity is measured by the following decrease in absorbance at 340 nm due to conversion of NADH to NAD$^+$ in 1 ml of reaction mixture, 8 mM sodium pyruvate, 0.15 mM NADH, 50 mM tris-chloride pH 7.5. One unit of enzyme activity is defined as that amount which oxidized 1 μmole of NADH per minute at 25° C.

The *Lactobacillus bulgaricus* according to the invention is also characterized by a more increased β-galactosidase (β-gal) activity than of the wild type strain Lfi5.

Advantageously, said β-galactosidase activity is higher than 200%, preferably higher than 500% of the β-galactosidae activity of the wild type strain Lfi5.

Advantageously, the β-galactosidase activity is higher than 300 units, preferably higher than 500 units of enzyme activity/10 ml culture.

The β-galactosidase activity is determined by the method of Miller J. H. (Experiments in molecular genetics, Cold Spring Harbor Laboratory N.Y., 1972).

50 μl of cell free extract is added in 1 ml of Z buffer, 0.1.M sodium phosphate pH 7.0, 10 mM KCl, 1 mM $MgSO_4$, 50 mM 2-mercaptoethanol, and equilibrated at 28° C. Prewarmed 200 μl ONPG is added and incubated at 28° C. for 20 minutes. The reaction is stopped by adding 0.5 ml $Na_2CO_3$ 1M.

The absorbance at 420 nm is measured. One unit of enzyme activity is defined as the amount that hydrolyzed 1 μmole of ONPG per minute at 28° C.

Preferably, the *Lactobacillus bulgaricus* according to the invention is characterized by a LDH activity versus β-galactosidase activity lower than 0,8; preferably lower than 0,3.

The *Lactobacillus bulgaricus* according to the invention (isolated mutants) presents pathways which direct more of the pyruvate towards the aroma pathways than the production of lactic acid.

Preferably, the *Lactobacillus bulgaricus* according to the invention is selected from the group consisting of the strains of *Lactobacillus bulgaricus* CNCM I-1348 and I-1349.

The strains are characterized by the following properties:

Origin: mutant isolated from a commercialized *L. bulgaricus* strain of the Nestlé collection;

Morphology: straight unflagellated Bacilli. No sporulation, $Gram^+$ microorganisms, catalase negative and optionally anaerobics;

Saccharide fermentation: lactic acid production from:
D-glucose
D-fructose
D-mannose
lactose;

Miscellaneous:
reduced activity of the LDH enzyme (lactate dehydrogenase)
texturating properties (exopolysaccharide production).

Mutants of *Lactobacillus bulgaricus* having reduced LDH activity will increase the production of aroma and flavor compounds. Analysis of the isolated mutants by comparing their LDH versus β-galactosidase activity (LDH/β-gal ratio) indicated which of the mutants are not only low in LDH activity (high production of aroma compound and low production of lactic acid) but in fact channeled more of the carbon flow (β-galactosidase activity) into the production of aroma and flavor compounds.

The present invention concerns also a food composition comprising said *Lactobacillus bulgaricus*.

Advantageously, the said food composition is a yoghurt or yoghurt like product, preferably a mild yoghurt or mild yoghurt like products, comprising the *Lactobacillus bulgaricus* according to the invention and *Streptococcus thermophilus*.

The yoghurt or the yoghurt like product according to the invention are characterized by an increased aroma and flavor production and a reduction of acidification and post-acidification.

DESCRIPTION OF A PREFERRED EMBODIMENT OF THE INVENTION

Figure 1:
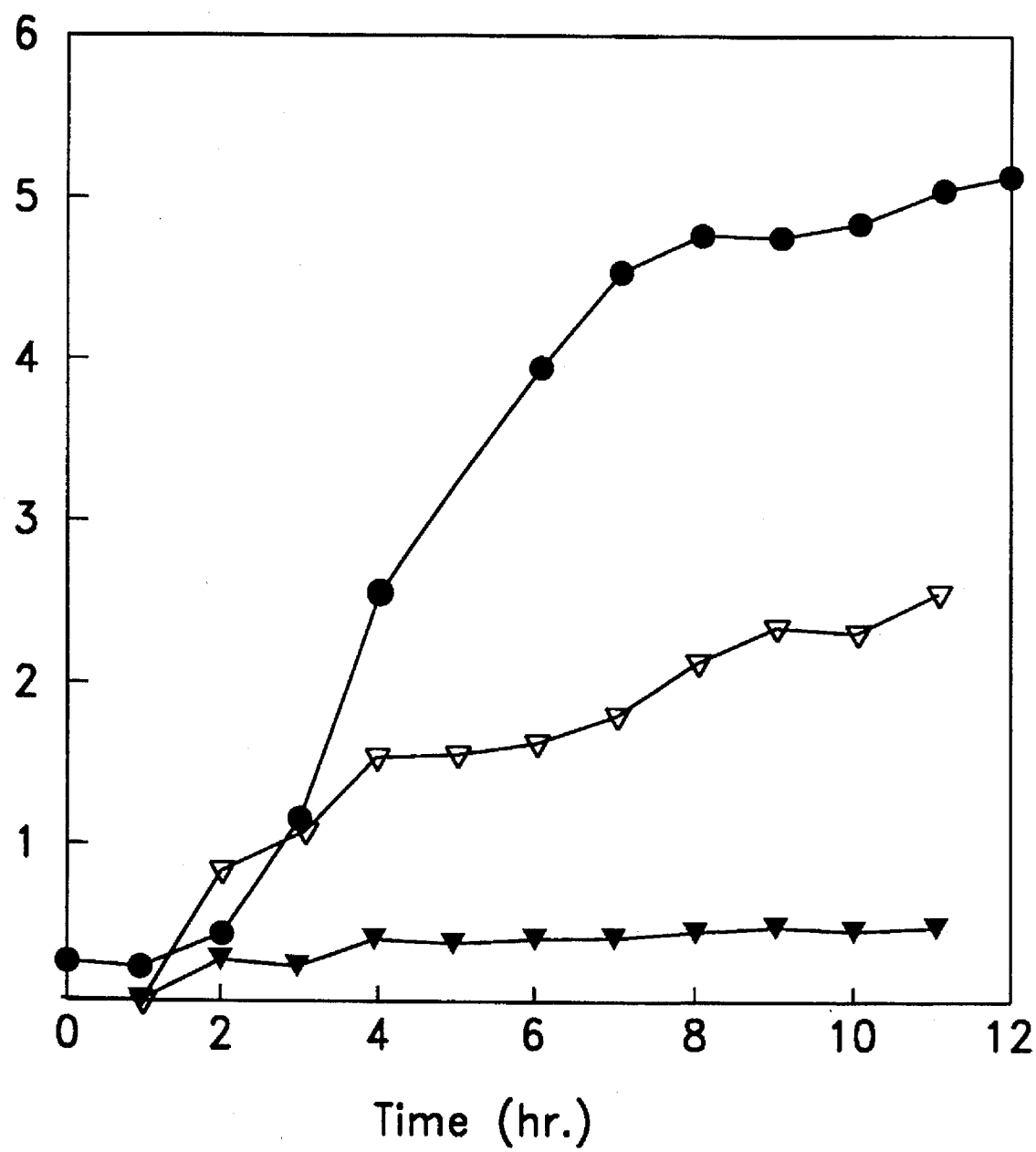
FIG. 1 represents the growth behaviors (● OD 600, ▽ LDH/protein×100, ▼ LDH/β gal) of the *L. bulgaricus* Lfi5.

A. Optimization of mutagenesis on *Lactobacillus bulgaricus* Media and bacteria

*Lactobacillus bulgaricus* is grown in 10 ml Lactobacillus MRS broth (0.5% yeast extract, 1% meat extract, 1% peptone, 0.1% Tween 80, 0.2% ammonium citrate, 0.5% sodium acetate, 0.2% $K_2HPO_4$, 0.01% $MgSO_4$, 0.005% $MnSO_4$) (x) at 42° C. MRS agar plate contains MRS with 15 g agar per 1 liter. MRS X-Gal agar plates contains X-Gal(5-bromo-4-chloro-3-indolyl-β-D-galactopyranoside) at 25 μg/ml.

The Mutagenesis of *L. bulgaricus* strain Lfi5 are obtained with ultraviolet light Mutagenesis or by N-methyl-N'-nitro-N-nitrosoguanidine (MNNG) mutagenesis according to the method of Silhavy (T. J. Silhavy, M. L. Berman and W. Enquist (1984), Experiments with gene fusions: Cold Spring Harbor Laboratory).

Mutation frequency of MNNG mutagenesis is 7 times higher than that of UV light mutagenesis.

B. Screening of low activity mutants of lactate dehydrogenase

Overnight cultures of mutagenized cells are diluted and plated onto MRS agar plate and incubated at 42° C. overnight. Single colonies are picked, inoculated in 250 μl MRS broth in microtites plates (FALCON 3072) and grown at 42° C. overnight. 50 μl of each cell suspension are dot-blotted onto membrane filter (Dupont GeneScreen). The filter is placed on 3M Whatman filter saturated with the cell lysis solution, 1 mg/ml lysozyme and 50 μg/ml mutanolysin in water, and incubated at 37° C. for 30 min. Then the filter is exposed in chloroformvapor for 30 minutes, airdried and frozen at −80° C. for 30 minutes. It is washed with 50 mM tris-chloride buffer pH 8.0 to remove cell debris. The washed filter is soaked for 1–4 minutes in staining solution, 134 mM D-lactic acid sodium salt, 2 mM iodonitrotetrazolium chloride, 1.4 mM $NAD^+$, 0.5 mM N-methylphenazonium methyl sulfate, 50 mM trischloride pH 8.0. To stop the reaction, the filter is washed with 0.1N HCl. The activity of the Lactate dehydrogenase is relative to the intensitivity of the red coloring of the individual colonies on the plates. Cells showing weak signals are transfered to 10 ml fresh MRS broth and incubated at 42° C. overnight. The cells are harvested by centrifugation and resuspended in 1 ml MRS broth containing 15% glycerol. Cell suspensions are stored at −80° C.

Preparation of cell free extracts

Prewarmed 10 ml fresh MRS broth containing 2% lactose is inoculated with 2% of an overnight culture and incubated at 42° C. for 7 hours. The cells are harvested by centrifugation and washed twice with the buffer, 50 mM trischloride pH 8,0, 100 mM NaCl, 2 mM EDTA, 1 mM PMSF, 1 mM DTT and resuspended in 1 ml of the buffer. 100 µl of 10 mg/ml lysozyme solution and 50 µl of 1 mg/ml mutanolysin solution are added and incubated at 37° C. for 10 minutes. Cell debris is removed by centrifugation at 12,000 rpm for 30 minutes.

Lactate dehydrogenase assay

Lactate dehydrogenase activity is measured by the following decrease in absorbance at 340 nm due to conversion of NADH to $NAD^+$, in 50 mM tris-chloride pH 7.5. One unit of enzyme activity is defined as the amount with oxidized 1 µmole of NADH per minute at 25° C.

β-galactosidase assay

β-galactosidase activity is determined by the method of Miller (Experiments in molecular genetics, Cold Spring Harbor Laboratory N.Y., 1972). 50 µl of cell free extract is added in 1 ml of Z buffer, 0.1M sodium phosphate pH 7.0, 10 mM KCl, 1 mM $MgSO_4$, 50 mM 2-mercaptoethanol, and equilibrated at 28° C. Prewarmed 200 µl ONPG is added and incubated at 28° C. for 20 minutes. The reaction is stopped by adding 0.5 ml 1M $Na_2CO_3$. Absorbance at 420 nm is measured. One unit of enzyme activity is defined as the amount that hydrolyzed 1 µmole of ONPG per minute at 28° C.

Protein assay

Total protein concentration is determined by the dye binding assay of Bradford (M. M. Bradford, (1976), Anal. Biochem, 72: 248–254) using the kit of Bio-Rad.

*Lactobacillus bulgaricus*, Lfi5 and YL30 are mutagenized as described before (Table 1). 3388 colonies of MNNG mutagenized cells of Lfi5, 616 colonies of UV mutagenized cells of Lfi5 and 1078 colonies of MNNG mutagenized cells of YL30 are picked up and tested. 152 colonies are identified as LDH mutants in this first screening with the membrane assay. FIG. 1 presents an example of such a result.

Candidates identified in this screening are used to measure the LDH activity. Each candidate is grown in MRS with 2% lactose media, and harvested at the early stationary log-phase that provide the highest activity. The cells are lysed by incubation with mutanolysin and lysozyme. Other methods are tested as well. They are summarized in Table 2. The glass beads method is described by Abbondi (M. E. Abbondi, S. Pandian, G. Trepanier, R. E. Simard and B. H. Lee (1991), J. Food Sci., 56: 948–953).

Figure 2A:
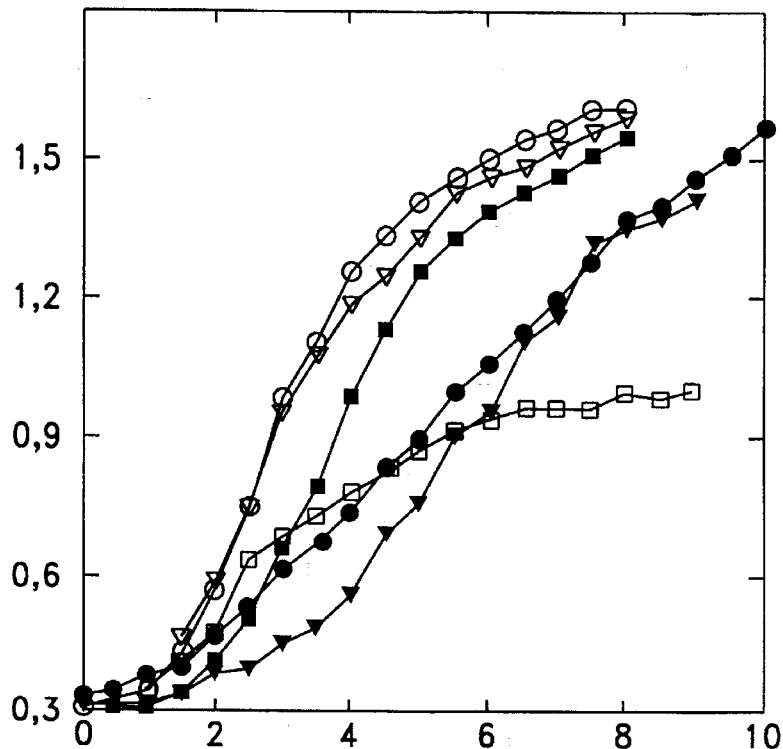
FIG. 2 represents the growth behaviors of LDH low mutants on Lfi5 (○ Lfi 5, ● KTL50, ▽ KTL6, ▼ KTL8, □ KTL52, ■ KTH1).
Figure 2B:
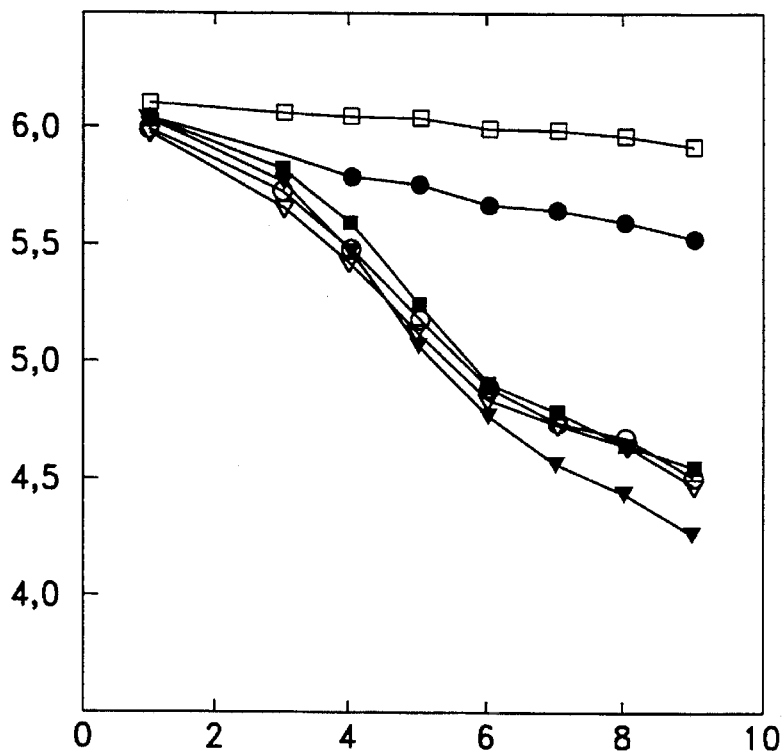
Figure 3:
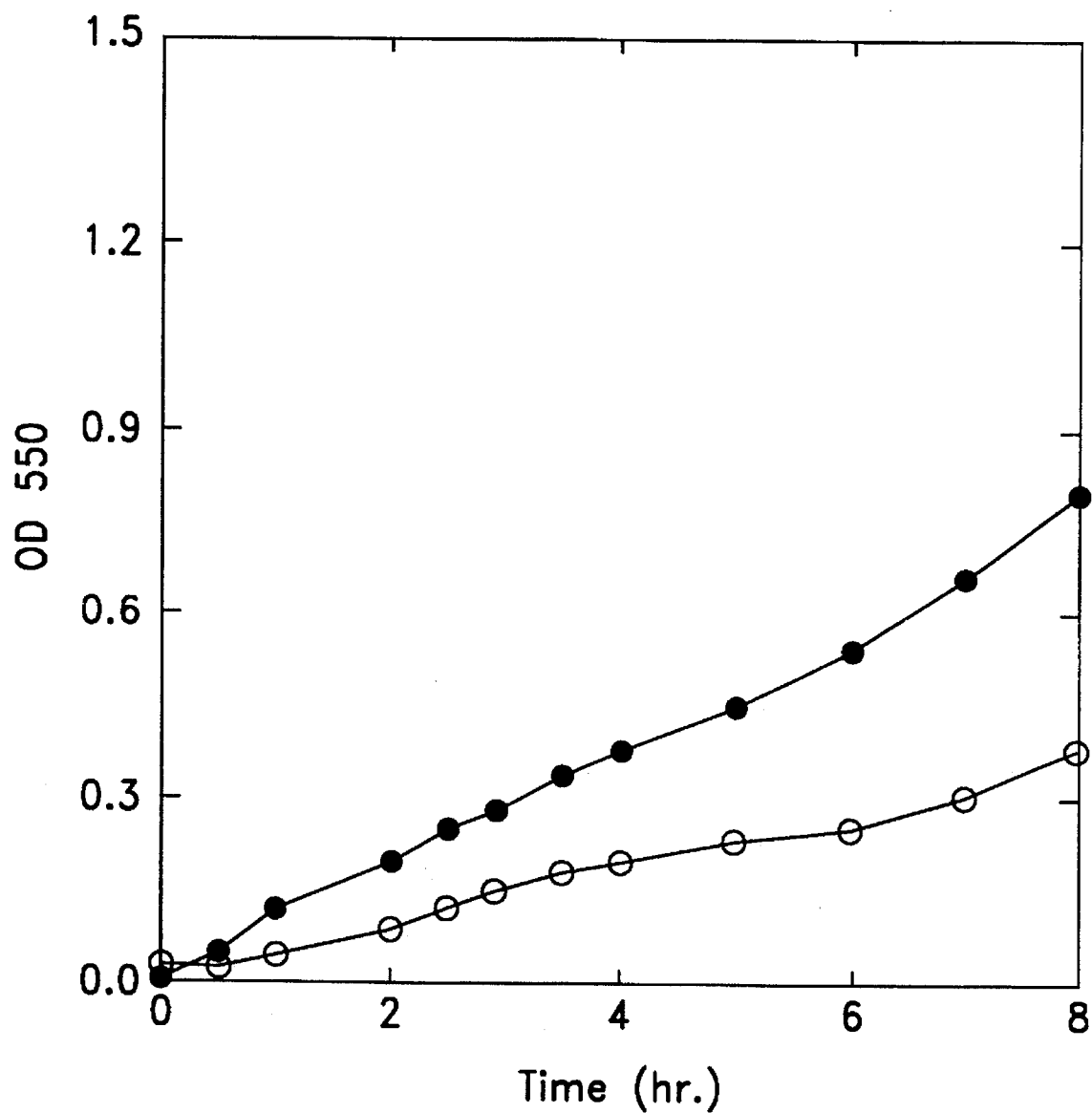
FIG. 3 represents the effects of LDH in the medium to KTL 50 (○ KTL50 without LDH, ● KTL50 with LDH).

The activity of LDH is determined by the specific activity of total LDH units per total cellular protein of the cell free extract. The specific activity of LDH is continuously increased with the cell growth (FIG. 2). Since β-galactosidase is also an important enzyme of the glycolysis pathway, the ratio LDH per β-galactosidase activity should be constant. In fact, the ratio is almost stable from the mid-log phase to the early stationary phase. The mutants are identified by the evaluation of this ratio, total LDH versus β-galactosidase activity. The results are shown in Table 3.

The mutants are classified in six groups. The mutants of Group 1 indicate low total LDH activity, below the average minus 20%, but keep the normal level of β-gal activity. Their low LDH / β-galactosidase ratio is only due to the low LDH mutations. Group 2 also has low LDH activity, but their β-gal activity is more than the average of the wild type.

The mutants in Group 1, 2, 3 and 4 are the low LDH mutants. They have low LDH / β-galactosidase ratios and low total LDH activities. 13 mutants of Lfi5 and 10 mutants of YL30 are categorized in these groups. The frequency of mutation for each strain is $3.8 \times 10^{-3}$ and $8.3 \times 10^{-3}$ respectively.

KTL50, 78, 81, KTY41, 18 and 46 have lower LDH / β-galactosidase ratios (1:100 to 1:200) than the wild type strain. Moreover, their total β-gal activity is conserved.

Mutants of Group 5 show normal activity. However, their β-gal activity is increased.

KTL50 and KTH1 of Group 1, KTL6 of Group 2, KTL52 of Group 3 and KTL8 of Group 5 are examined for growth behavior and post acidification.

C. Characterization of LDH low mutants
Acidification of LDH low activity mutants

Growth Curve

Mutants are inoculated at 2% in pyrex culture tubes (16×150 mm) containing 17 ml prewarmed MRS with 2% lactose and incubated at 42° C. The optical density at 550 nm are monitored every 30 minutes.

pH curve

Mutants are inoculated at 2% in 10 ml prewarmed MRS broth with 2% lactose and incubated at 42° C. pH is monitored every 30 minutes.

Post-acidification of LDH low activity mutants in mixed culture yoghurt assays The starter culture inoculum consists of 1.5% Sfi16, 1.5% Sfi21 standard commercial strains of *S. thermophilus* and 0.8% of the candidate *L. bulgaricus*. Yoghurts are prepared from 150 ml pasteurized milk, 3% reconstituted skim milk 1.5% milk fat, inoculated with the above mixed culture. The cultures are grown at 40° C. until they reach a pH value of about 4.6. They are then cooled to 4° C. overnight and stored at 4° C. or 12° C. for 26 days. The pH value, organoleptic qualities and cell numbers are monitored after 7 days, 14 days and 26 days of incubation.

The results are shown in Table 4. Yoghurt stored at 4° C. shows only weak post-acidification after 26 days. Mutants and wild type strain kept their pH value above 4.3. There are small differences of pH value (about 0.1) between wild types and LDH low mutants. The culture stored at 12° C. shows post-acidification. While wild type strain Lfi5 acidifies the pH value to 4.0 after 26 days, the pH of LDH low mutants, KTL50 and KTH1, are still kept at 4.2.

The KTL1, 18 and 42 *Lactobacillus bulgaricus* strains are filed according to the Budapest treaty in the Collection Nationale de Cultures de Microorganismes (CNCM), Institut Pasteur, 28, rue du Docteur Roux, 75024 Paris Cedex 15, France, under the numbers CNCM I-1348, CNCM I-1349 and CNCM I-1350.

The invention will be illustrated by the following examples.

Example I

Yeast extract (0.1% v/v) was added to 500 ml 9% (w/v) skim milk powder. The resulting solution was autoclaved at 121° C. for 15 minutes, followed by addition of 10% (v/v) of an active culture of *L. bulgaricus* strain CNCM I-1348 (KTL 1) containing about $5 \times 10^8$ bacteria/$cm^3$.

By incubating this mixture for 4 hours at 40° C., a leaven containing around $2.5 \times 10^8$ microorganisms/cm³ is obtained.

According to the same method, a leaven containing around $5 \times 10^8$ thickening *S. thermophilus*/cm³ from an active culture of a commercialized strain is obtained.

Skim milk powder (3% w/v) was added to a milk standard batch containing 1.5% fat. The resulting solution was pasteurized for 30 minutes at 90° C., followed by addition of 1% (v/v) of the *L. bulgaricus* strain CNCM I-1348 (KTL 1)leaven and 3% (v/v)of the commercialized strain of *S. thermophilus*.

After a weak stirring, the preparation is disposed in cans and incubated for 4h20 at 40° C. until a pH of 4.62.

The yoghurt obtained presents a good texture and a very interesting taste for this type of product. Around $1 \times 10^9$ *S. thermophilus*/cm³ and around $1 \times 10^8$ *L. bulgaricus*/cm³ are numbered.

Example II

As in Example 1, a leaven of *L. bulgaricus* CNCM I-1349 (KTL 18) is prepared, containing around $3 \times 10^8$ microorganisms/cm³ after 8 hours after incubation.

With the addition of 1% of a *L. bulgaricus* CNCM I-1349(KTL 18) leaven, and 3% *S. thermophilus* leaven to a standard milk batch (as described in Example 1), a yoghurt of pH 4.61 is obtained.

After 4h40 of incubation at 40° C., around $8 \times 10^8$ *S. thermophilous* and around $1 \times 10^7$ *L. bulgaricus*/cm³ are numbered.

This yoghurt of very unctuous texture presents a very interesting fresh milk taste.

Example III

The strain of *L. bulgaricus* CNCM I-1350 (KTL 42) is obtained according to the process described in the above examples.

After 5 hours, a leaven containing around $5 \times 10^8$ microorganisms/cm³ is obtained.

According to the example I, a yoghurt of pH 4.62 is obtained after 3h45 incubation. Around $1 \times 10^9$ *S. thermophilus*/cm³ and around $2 \times 10^8$ *L. bulgaricus*/cm³ are numbered.

In addition of a very sweet texture, it presents a very strong typical yoghurt taste.

These products are submitted to a taste preservation test at 4° C. and 12° C., said tests comprising a pH testing and taste testing after respectively 1, 7, 14 and 26 stockage days.

These results are presented in table 5.

Comparative test

As witness, the original strain of the three mutants CNCM I-1348, CNCM I-1349 and CNCM I-1350 (KTL 1, 18, 42) is used to obtain a yoghurt according to the method described in Example I.

After 3h45 of incubation, a yoghurt with a pH of 4.54 and containing around $1 \times 10^9$ *S. thermophilus*/cm³ and around $2 \times 10^8$ *L. bulgaricus*/cm³ is obtained.

TABLE 1

Results of the screening of the low LDH mutants

| Strain | Method of Mutagenesis | Total cell number | After first screening | After the second test |
|---|---|---|---|---|
| Lfi5 | MNNG | 3388 | 99 | 13 ($3.8 \times 10^{-3}$) |
| Lfi5 | UV | 616 | 7 | 0 (0) |
| YL30 | MNNG | 1078 | 46 | 10 ($9.3 \times 10^{-3}$) |

TABLE 2

Comparisons of the cell lysis methods

| Method of cell lysis | | Total LDH U/10 ml culture | Total β-gal U/10 ml culture |
|---|---|---|---|
| Mutanolysin + Lysozyme | 1 | 213.9 | 327.8 |
| | 2 | 214.5 | 319.0 |
| | Ave | 214.7 | 323.4 |
| Glass beads | 1 | 192.6 | 338.2 |
| | 2 | 125.8 | 203.3 |
| | Ave | 159.2 | 270.8 |
| Toluene | 1 | 20.8 | 144.2 |
| | 2 | 62.75 | 312.5 |
| | Ave | 41.8 | 228.4 |

TABLE 3.1

List of mutant on *Lactobacillus bulgaricus* Lfi5

| Strain name | LDH/ Gal | LDH U/10 ml cul. | Gal U/10 ml cul. | OD 550 at Havest. |
|---|---|---|---|---|
| Lfi5 | 0.426 | 229 | 541 | 1.23 |
| Group 1 (Low LDH) | | | | |
| KTL50 | 0.0013 | 0.5 | 412 | 0.82 |
| KTL78 | 0.031 | 11 | 359 | 1.12 |
| KTL81 | 0.035 | 14 | 402 | 1.11 |
| KTL83 | 0.102 | 52 | 509 | 1.16 |
| KTH1 | 0.300 | 110 | 368 | 1.12 |
| Group 2 (Low LDH, high β-gal) | | | | |
| KTL6 | 0.233 | 159 | 666 | 1.17 |
| KTH16 | 0.214 | 129 | 607 | |
| KTH18 | 0.295 | 172 | 583 | |
| Group 3 (Low LDH, low β-gal) | | | | |
| KTL52 | 0.159 | 17 | 106 | 0.65 |
| KTL53 | 0.288 | 52 | 182 | 0.94 |
| KTH5 | 0.300 | 12 | 40 | |
| KTH4 | 0.256 | 66 | 259 | |
| KTH7 | 0.294 | 78 | 266 | |
| Group 4 (High β-gal) | | | | |
| KTL8 | 0.213 | 217 | 1020 | 0.79 |
| KTL65 | 0.256 | 201 | 789 | 1.35 |
| KTL55 | 0.301 | 194 | 644 | 1.30 |
| KTH14 | 0.277 | 216 | 780 | |
| KTH17 | 0.297 | 221 | 744 | |
| Group 6 (Low β-gal) | 5.1213 | 182 | 36 | |
| KTL69 | | | | |

TABLE 3.2

List of mutants on Lactobacillus bulgaricus YL30

| Strain name | LDH/Gal | LDH U/10 ml cul. | Gal U/10 ml cul. | OD 550 at Havest. |
|---|---|---|---|---|
| YL30 | 0.314 | 181 | 574 | 1.30 |
| Group 1 (Low LDH) | | | | |
| KTY41 | 0.0002 | 0.2 | 650 | 1.00 |
| KTY18 | 0.007 | 3 | 441 | 0.91 |
| KTY46 | 0.0023 | 11 | 467 | |
| KTY1 | 0.102 | 46 | 454 | |
| KTY4 | 0.170 | 106 | 625 | |
| KTY19 | 0.172 | 113 | 659 | |
| KTY11 | 0.198 | 112 | 567 | |
| Group 2 (Low LDH, high β-gal) | | | | |
| KTY7 | 0.141 | 101 | 717 | 1.40 |
| KTY9 | 0.163 | 149 | 916 | |
| Group 4 (High β-gal) | 0.182 | 173 | 952 | 1.10 |
| KTY13 | | | | |
| Group 5 (Low LDH, Low β-gal) | 0.982 | 60 | 61 | 0.67 |
| KTY28 | | | | |
| Group 6 (Low β-gal) | 278.8 | 175 | 0.6 | |
| KTY8 | | | | |

TABLE 4

Post acidification of yoghurt cultures

| Strains | Incubation[1] | pH value after: at 4° C. / 12° C. | | | Cells[2] |
|---|---|---|---|---|---|
| | | 7 days | 14 days | 26 days | |
| Lfi5 | 3 h 35 | 4.40 | 4.34 | 4.32 | $4.0 \times 10^7$ |
| | | 4.20 | 4.06 | 4.05 | $9.0 \times 10^7$ |
| KTL50 | 4 h | 4.53 | 4.43 | 4.42 | $1.6 \times 10^7$ |
| | | 4.28 | 4.15 | 4.17 | $6.4 \times 10^7$ |
| KTH1 | 4 h 20 | 4.46 | 4.33 | 4.35 | $7.5 \times 10^7$ |
| | | 4.26 | 4.12 | 4.14 | $1.8 \times 10^8$ |
| KTL6 | 3 h 10 | 4.51 | 4.39 | 4.37 | $6.3 \times 10^7$ |
| | | 4.20 | 4.05 | 4.02 | $7.3 \times 10^7$ |
| KTL8 | 4 h 45 | 4.32 | 4.37 | 4.42 | $2.0 \times 10^5$ |
| | | 4.26 | 4.22 | 4.24 | $3.5 \times 10^6$ |
| KTL18 | 4 h 40 | 4.54 | 4.54 | 4.59 | $9.4 \times 10^6$ |
| | | 4.38 | 4.24 | 4.25 | $3.4 \times 10^6$ |

[1]Incubation time to reach pH 4.6: The yoghurt was then transferred and stored at 4 or 12° C.
[2]Cell counts of L. bulgaricus per ml yoghurt culture after 26 days

TABLE 5

| Example | Stockage | T° = 4° C. | | T° = 12° C. | |
|---|---|---|---|---|---|
| | | pH | degustation | pH | degustation |
| 1 | 1 day | 4.46 | Sweet, flavoring | 4.46 | Sweet, flavoring |
| | 7 days | 4.46 | Sweet, flavoring | 4.26 | Acid taste |
| | 14 days | 4.33 | Sweet, fresh | 4.12 | Acid |
| | 26 days | 4.35 | Sweet, fresh | 4.14 | Raw milk taste |
| 2 | 1 day | 4.65 | Sweet, light taste | 4.65 | Sweet, light taste |
| | 7 days | 4.65 | Sweet, light taste | 4.38 | Sweet, fresh milk |
| | 14 days | 4.54 | Sweet, light taste | 4.24 | Very sweet, fresh |
| | 26 days | 4.59 | Sweet, light taste | 4.25 | Very sweet, fresh and tasting of wood fruit |
| 3 | 1 day | 4.58 | Sweet, light | 4.58 | Sweet, light |
| | 7 days | 4.48 | Sweet, light | 4.22 | Sweet, strong yoghurt taste |
| | 14 days | 4.36 | Sweet, strong taste | 4.07 | Acid, lightly bitter |
| | 26 days | 4.38 | Sweet, strong taste | 4.07 | Acid, bitter |
| WITNESS | 1 day | 4.45 | Sweet, lightly bitter | 4.45 | Sweet, lightly bitter |
| | 7 days | 4.40 | Sweet, light | 4.22 | Sweet, strong yoghurt taste |
| | 14 days | 4.36 | Sweet, strong taste | 4.07 | Acid, lightly bitter |
| | 26 days | 4.38 | Sweet, strong taste | 4.07 | Acid, bitter |

The above examples show that mutants CNCM I-1348, CNCM I-1349 and CNCM I-1350 (KTL 1, 18 and 42) presenting a reduced LDH activity, can produce a yoghurt with very interesting texture, flavoring and post-acidification properties. In addition, very different tastes at very high pH can be obtained.

We claim:

1. A mutagenized *Lactobacillus Bulgaricus* having a lactate dehydrogenase activity to β-galactosidase activity ratio lower than 0.3 and lactate dehydrogenase activity lower than 150 units of enzyme activity/10 ml culture.

2. A mutagenized *Lactobacillus bulgaricus* according to claim 1, wherein said lactate dehydrogenase activity is lower than 50% of the lactate dehydrogenase activity of *Lactobacillus bulgaricus* YL30.

3. A mutagenized *Lactobacillus bulgaricus* according to claim 2, wherein said lactate dehydrogenase activity is lower than 10% of the lactate dehydrogenase activity of *lactobacillus bulgaricus* YL30.

4. A mutagenized *Lactobacillus bulgaricus* according to claim 1 having β-galactosidase activity higher than 300 units of enzyme activity/10 ml culture.

5. A mutagenized *Lactobacillus bulgaricus* according to claim 4, wherein said β-galactosidase activity is higher than 500 units of enzyme activity/10 ml culture.

6. A mutagenized *Lactobacillus bulgaricus* according to claim 1, wherein said *Lactobacillus bulgaricus* is selected from the group consisting of the strains of *Lactobacillus bulgaricus* CNCM I-1348 and CNCM I-1349.

7. *Lactobacillus bulgaricus* according to claim 1, wherein said lactate dehydrogenase activity is lower than 10% of the lactate dehydrogenase activity of a *Lactobacillus bulgaricus* wild type strain.

8. *Lactobacillus bulgaricus* according to claim 3 having β-galactosidase activity higher than 500% of the β-galactosidase activity of a *Lactobacillus bulgaricus* wild type strain.

9. *Lactobacillus bulgaricus* according to claim 4, having β-galactosidase activity higher than 300 units of enzyme activity/10 ml culture.

* * * * *